US008551967B2

(12) United States Patent
Ferro et al.

(10) Patent No.: US 8,551,967 B2
(45) Date of Patent: Oct. 8, 2013

(54) FORMULATIONS WITH ANTI-TUMOUR ACTION

(75) Inventors: Laura Iris Ferro, Milan (IT); Massimo Iacobelli, Milan (IT); Paul Richardson, Wellesley, MA (US)

(73) Assignee: Gentium SpA, Villa Guardia (Como) (IT)

( * ) Notice: Subject to any disclaimer, the term of this patent is extended or adjusted under 35 U.S.C. 154(b) by 585 days.

(21) Appl. No.: 11/366,243

(22) Filed: Mar. 2, 2006

(65) Prior Publication Data

US 2006/0211646 A1 Sep. 21, 2006

Related U.S. Application Data

(63) Continuation-in-part of application No. PCT/EP2004/009723, filed on Aug. 27, 2004.

(60) Provisional application No. 60/539,344, filed on Jan. 28, 2004.

(30) Foreign Application Priority Data

Sep. 5, 2003 (IT) .......................... MI2003A001714

(51) Int. Cl.
*A61K 48/00* (2006.01)
*C07H 21/04* (2006.01)

(52) U.S. Cl.
USPC ........................................ 514/44 R; 536/23.1

(58) Field of Classification Search
None
See application file for complete search history.

(56) References Cited

U.S. PATENT DOCUMENTS

| | | | | |
|---|---|---|---|---|
| 3,770,720 A | 11/1973 | Butti | ................................ | 514/44 |
| 3,829,567 A | 8/1974 | Butti | ................................ | 514/44 |
| 3,899,481 A | 8/1975 | Butti | ................................ | 536/25 |
| 4,693,995 A | 9/1987 | Prino | ................................ | 514/44 |
| 4,694,134 A | 9/1987 | Ross | ................................ | 219/63 |
| 4,853,221 A * | 8/1989 | Elslager et al. | ................ | 424/649 |
| 4,985,552 A | 1/1991 | Fedeli | ................................ | 536/25 |
| 5,081,109 A | 1/1992 | Ulutin | ................................ | 514/44 |
| 5,223,609 A | 6/1993 | Fedeli | ................................ | 536/23 |
| 5,646,127 A | 7/1997 | Lanzarotti | | |
| 5,646,268 A | 7/1997 | Lanzarotti | | |
| 5,919,772 A | 7/1999 | Szyf | | |
| 5,977,083 A | 11/1999 | Burcoglu | | |
| 6,046,172 A | 4/2000 | Ennio | | |
| 2003/0013669 A1 | 1/2003 | Burcoglu | ........................ | 514/44 |
| 2004/0248834 A1 | 12/2004 | Klinman et al. | | |

FOREIGN PATENT DOCUMENTS

| | | |
|---|---|---|
| DE | 19740384 | 3/1999 |
| EP | 0558883 | 9/1993 |
| EP | 1550462 A1 | 7/2005 |
| EP | 1872787 A1 | 1/2008 |
| WO | WO 98/48843 * | 11/1998 |
| WO | 98/54313 | 12/1998 |
| WO | 9957153 A1 | 11/1999 |
| WO | 0074634 A2 | 12/2000 |
| WO | WO 02/053700 A2 * | 7/2002 |
| WO | 03004705 A1 | 1/2003 |
| WO | WO 03/101468 | 12/2003 |
| WO | WO 2004/003166 | 1/2004 |
| WO | 2004028516 A2 | 4/2004 |
| WO | 2004078922 A2 | 9/2004 |
| WO | 2006/094916 | 9/2006 |
| WO | 2006/094917 | 9/2006 |
| WO | 2008000549 A1 | 1/2008 |
| WO | 2008125424 A1 | 10/2008 |

OTHER PUBLICATIONS

Gura (Science, 1997, 278:1041-1042).*
Kaiser (Science, 2006, 313, 1370).*
Chopra et al. (British J. of Haematology, Dec. 2000;111(4):1122-9).*
National Library of Medicine—Medical Subject Heading (defibrotide, 2009 MeSH).*
PubChem Substance (defibrotide, SID 51091757, Mar. 11, 2009).*
DrugBank (Defibrotide, http://www.drugbank.ca/cgi-bin/getCard.cgi?CARD=DB04932.txt, Oct. 21, 2007).*
Palmer et al. (Drugs, 1993 45:259-294).*
Imaginis.com (clinical trial, Aug. 30, 2000).*
Mitsiades Constantine S. et al, "Defibrotide (DF) has anti-neoplastic activity against multiple myeloma: Clinical implications for the incorporation of DF in cytotoxic chemotherpeutic regimes", Blood, vol. 102, No. 11, Nov. 16, 2003, p. 693a.
Eissner Guenther et al., "Fludarabine induces apoptosis, activation, and allongenicity in human endothelial and epithelial cells: Protective effect of defibrotide", Blood, vol. 100, No. 1, Jul. 1, 2002, pp. 334-340.
Carlo-Stella, C., Di Nicola, M., Magni M., et al.,Defibrotide in Combination with Granulocyte Colony-stimulating Factor Significantly Enhances the Mobilization of Primitive and Committed Peripheral Blood Progenitor Cells in Mice. Cancer Research, 2002, 62:6152-6157 (Nov. 1, 2002).
Hazlehurst, L., Damiano, J., Buyuksal, I., Pledger, W.J., Dalton, W.S., Adhesion to fibronectin via b1 integrins regulates p27 kip1 levels and contributes to cell adhesion mediated drug resistance (CAM-DR). Oncogene, 2000; 19:4319-4327.
Richardson, P.G., Elias, A.D., Krishnan, A., et al. Treatment of severe veno-occlusive disease with defibrotide: compassionate use results in response without significant toxicity in a high-risk population. Blood, 1998; 92: 737-44.
Richardson, P., Murakami, C., Jin, Z., et al., Multi-institutional use of defibrotide in 88 patients after stem cell transplantation with severe veno-occlusive disease and multi-system organ failure: response without significant toxicity in a high risk population and factors predictive of outcome. Blood, 2002; 100(13):4337-4343.
Falanga, A., Vignoli, A., Marchetti, M., Barbui, T., Defibrotide reduces procoagulant activity and increases fibrinolytic properties of endothelial cells. Leukemia, 2003; in press.
Abdalla, S .A. , et al . (1999) Prognostic relevance of microvessel density in colorectal tumours. Oncol. Rep., 6, 839-842.

(Continued)

*Primary Examiner* — Peter J Reddig
(74) *Attorney, Agent, or Firm* — Fredrikson & Byron, P.A.

(57) ABSTRACT

The use of defibrotide as an anti-tumor agent, alone or in combination with other active ingredients with anti-tumor action, is described.

14 Claims, 2 Drawing Sheets

(56) References Cited

OTHER PUBLICATIONS

Andersen, N. F., et al. (2005) Syndecan-1 and angiogenic cytokines in multiple myeloma: correlation with bone marrow angiogenesis and survival. Br. J.Haematol., 128, 210-217.

Bostwick, D.G. & Iczkowski, K.A. (1998) Microvessel density in prostate cancer: prognostic and therapeutic utility. Semin. Urol. Oncol., 16, 118-123.

Fernandez, P. B., et al. (2001) Dendritic cells derived from peripheral monocytes express endothelial markers and in the presence of angiogenic growth factors differentiate into endothelial-like cells. Eur. J. Cell Biol., 80, 99-110.

Folkman, J., et al. (1971) Isolation of a tumor factor responsible for angiogenesis. J. Exp.Med., 133, 275-288.

Fontanini, G., et al. (1995) Microvessel count predicts metastatic disease and survival in non-small cell lung cancer. J.Pathol., 177, 57-63.

Guba, M., et al. (2002) Rapamycin inhibits primary and metastatic tumor growth by antiangiogenesis: involvement of vascular endothelial growth factor. Nat. Med., 8, 128-135.

Guba, M., et al. (2005) Rapamycin induces tumor-specific thrombosis via tissue factor in the presence of VEGF. Blood.

Hanahan, D. & Folkman,J. (1996) Patterns and emerging mechanisms of the angiogenic switch during tumorigenesis. Cell, 86, 353-364.

Hasan, J., et al. (2002) Intra-tumoural microvessel density in human solid tumours. Br. J. Cancer, 86, 1566-1577.

Helmlinger, G., et al. (1997) Interstitial pH and pO2 gradients in solid tumors in vivo: high-resolution measurements reveal a lack of correlation. Nat. Med., 3, 177-182.

Kainz, C, et al. (1995) Prognostic value of tumour microvessel density in cancer of the uterine cervix stage IB to HB. Anticancer Res., 15, 1549-1551.

Mitsiades Constantine S. dt al: "Defibrotide (DF) Targets Tumor-Microenvironmental Interactions and Sensitizes Multiple Myeloma and Solid Tumor Cells to Cytotoxic Chemotherapetuics" Blood, W.B. Saunders Company, Orlando, FL, US, vol. 104, No. 11, Part 1, Nov. 2004, p. 85A, XPOO9067860 & 46th Annual Meeting of the American Society of Hematology; San Diego, CA, USA, Dec. 4-7, 2004. ISSN: 0006-5971.

Morabito, A., et al. (2004) Antiangiogenic strategies, compounds, and early clinical results in breast cancer. Crit Rev. Oncol .Hematol., 49, 91-107.

Podar, K. & Anderson, K. C. (2005) The pathophysiologic role of VEGF in hematologic malignancies: therapeutic implications. Blood, 105, 1383-1395.

Staton, C.A., et al. (2004) Current methods for assaying angiogenesis in vitro and in vivo. Int. J. Exp. Pathol., 85, 233-248.

Sun, H. C, et al. (1999) Microvessel density of hepatocellular carcinoma: its relationship with prognosis. J. Cancer Res. Clin. Oncol., 125, 419-426.

van 't Veer, L. J., et al.(2002) Gene expression profiling predicts clinical outcome of breast cancer. Nature, 415, 530-536.

Verheul, H.M., et al. (2004) Are tumours angiogenesis-dependent? J. Pathol., 202, 5-13.

Weidner, N., et al. (1992) Tumor angiogenesis: a new significant and independent prognostic indicator in early-stage breast carcinoma. J. Natl. Cancer Inst., 84, 1875-1887.

Xiangming, C., et al. (1998) Angiogenesis as an unfavorable factor related to lymph node metastasis in early gastric cancer. Ann. Surg. Oncol., 5, 585-589.

Pellegatta F et al., "The anti-ischemic drugs defibotide and oligotide analogously inhiibit leukocyte-endothelial cell adhesion in vitro," Transplant International vol. 9, No. Suppl 1, 1996, pp. 420-424.

Marni A. et al., "Anti-ischemic effect of oligotide treatment in rat kidney: comparison with the effect of nifedipine and isosorbide dinitrate," Transplantation Proceedings, vol. 28, No. 1, 1996, pp. 303-303.

Conde-Knape K. et al., "Heparan sulfate proteoglycans in experimental models of diabetes: a role for perlecan in diabetes complications," Diabetes Meta Res Rev; 2001 (14)412-421.

Dempsey L. et al., "Heparanase expression in invasive trophoblasts and acute vascular damage," Glycobiology, 2000; (10), n. 55, pp. 467-475.

Han J. et al., "Endothelial cell injury by high glucose and heparanase is prevented by insultin, heparin and basic fibroblast growth factor," Cardiovascular Diabetology, 2005; (4):1-12.

Levidiotis, V. et al., "Heparanase inhibition reduces proteinnuria in a model of accelerated anti-glomerular basement membrane antibody disease," Nephrology, 2005; (10), n. 2, pp. 167-173(7).

Levidiotis V. et al., "Heparanase is involved in the pathogenesis of proteinnuria as a result of glomerulonephritis" J Am Soc Nephrol; 2004 (15):68-7.

Levidiotis V., et al., "A synthetic heparanase inhibitor reduces proteinuria in passive heymann nephritis," J Am Soc Nephrol; 2004 (15):2882-2892.

Levidiotis V., et al., "Increased expression of heparanase in puromycin aminonucleoside nephrosis," Kidney Int, 2001; (60):1287-1296.

Maxhimer, J et al., "Heparanase-1 gene expression and regulation by high glucose in renal epithelial cells," Diabetes 2005; (54):2172-2178.

Parish, C.R. et al., "Heparanase: a key enzyme involved in cell invasion," Biochem. Biophys. Acta., 2001; (1471): M99-M108.

Tamsma JT et al., "Expression of glomerular extracellular matrix components in human diabetic nephropathy: decrease of heparan sulphate in the glomerular basement membrane," Diabetologia; 1994 (37):313-320.

van den Born J et al., "Distribution of GBM heparan sulfate proteoglycan core protein and side chains in human glomerular diseases," Kidney Int; 1993 (43):454-463.

Vlodavsky, I. et al., "Mammalian heparanase: Gene cloning, expression and function in tumor progression and metastasis," Nature Medicine, 1999; (5):793-802.

Vlodavsky, I. et al., "Molecular properties and involvement of heparanase in cancer metastasis and angiogenesis," Clin. Invest. 2001; (108):341-347.

Voskoglou-Nomikos et al. (Clinical Cancer Research, 2003, 9, 4227-4239.

Kelland et al. (European Journal of Cancer, 2004, 40, 827-836.

Kerbet et al. (Cancer Biology & Therapy 2: 4 suppl. 1, S134-139, 2003.

Esau et al. (Advanced Drug Delivery Reviews, 59: 101-114, 2007.

Trichon BH et al., "Acute coronary syndromes and diabetes mellitus," Diab. Vasc, Dis. Res. May 2004;1(1):23-32.

Vingolo E M, et al., "Treatment of nonproliferative diabetic retinopathy with Defibrotide in noninsulin-dependent diabetes mellitus: A pilot study," ACTA Ophthalmologica Scandinavica, Hvidovre, DK, vol. 77, No. 3, 1999, pp. 315-320.

Davi, G et al., "Effects of Defibrotide on Fibrinolytic Activity in Diabetic Patients with Stable Angina Pectoris," Thromobsis Research, vol. 65, No. 2, 1992, pp. 211-220.

Belcaro, G. et al., "Fibrinolytic Enhancement in Diabetic Microangiopathy with Defibrotide," Angiology, Westminster Publications, Inc., Glen Head, NY, US, vol. 43, No. 10, 1992, pp. 793-800.

Belcaro, G., et al., "Laser Doppler Flowmetry and Transcutaneous Oximetry Evaluation in Microangiopathic Diabetic Patients Treated with Defibrotide," Current Therapeutic Research, Excerpta Medica, Treton, NJ, US, vol. 45, No. 5, 1989, pp. 726-732.

Davis, S., "Insulin, Oral Hypoglycemic Agents, and the Pharmacology of the Endocrine Pancreas," Goodman & Gilman's The Pharmacological Basis of Therapeutics, Chapter 60, Section XII, Hormones and Hormone Antagonists, McGraw-Hill, 2006, pp. 1613-1656.

Araus-Pacheo C. et al., "The treatment of hypertension in adult patients with diabetes," Diabetes car, Jan. 2002;25 (1):134-47.

Kochar DK et al., "Sodium valproate for painful diabetic neuropathy: a radonmized double-blind placebo-controlled study," Qjm. Jan. 2004;97(1):33-8.

Argoff CE et al., "Consensus guidelines: treatment planning and options. Diabetic peripheral neuropathic pain," Mayo Clinic proceedings. Apr. 2006;81(4 Suppl):S12-25.

Fong DS, et al., "Diabetic retinopathy. Diabetes care," Oct. 2004;27(10):2540-53.

(56) References Cited

OTHER PUBLICATIONS

Koehl, G.E. et al, "An endothelium protecting and stabilizing drug, has an anti-angiogenic pootential in vitro and in vivo," Cancer Bioloty & Therapy, 6:5, 686-690, 2007.

Mitsiades, C.S. et al, "Preclinical studies in support of defibrotide for the treatment of multiple myeloma and other neoplasias," Clin. Cancer Res. 2009; 15: 1210-1221.

Kornblum et al, "Defibrotide, a polydisperse mixture of single-stranded phosphodiester oligonucleotides with lifesaving activity in severe hepatic veno-occlusive disease; Clinical outcomes and potential mechanisms of action," Oligonucleotides, vol. 16, No. 1, 2006, pp. 105-114.

Becker et al., "Organikum" 1990, Deutscher Verlag der Wissenschften, Berlin, 2 pgs.

Stephen, S. et al., "Effect of Rapamycin Alone and in Combinatino with Antiangiogenesis Therapy in an Orthotopic Model of Human Pancreatic Cancer," Clinical Cancer Research 6993, vol. 10, 6993-7000, Oct. 13, 2004.

Algire,G."An Adaption of the Transparent-Chamber Technique to the Mouse," Journal of the National Cancer Institute, vol. 4, Aug. 1943, No. 2.

Burra, P. et al., "Warm Hepatic Ischemia in Pigs: Effects of L-Arginine and Oligotide Treatment," Journal of Investigative Surgery, 14:303-312, 2001.

Cao, Y., "Tumor angiogenesis and therapy," Biomedicine & Pharmacotherapy 59 (2005) S340-S343.

Murohara, T. et al., "Cardioprotective actions of oligotide, a single stranded polydeoxyribunucleotide complex, in myocardial ischaemia and reperfusion injury,"British Journal of Pharmacology (1996) 177, 1000-1008.

Folkman et al, "Switch to the Angiogenic Phenotype during Temuorigenesis," Mufishtage Cardinogenesis, C.C. Harris ete al. (EDS.), Apan Sci. Soc. Press. Tokyo/GRC Press, Boca Raton, pp. 339-347, 1992.

Maeshima, Y. et al., "Identification of the Anti-angiogenic Site within Vascular Basement Membrane-derived Tumstatin," The Journal of Biological Chemistry, vol. 276, No. 18, Issue of May 4, pp. 15240-15248, 2001.

Mondesire, W. et al., "Targeting Mammalian Target of Rapamycin Synergistically Enhances Chemotherapy-Induced Cytotoxicity in Breast Cancer Cells," Clinical Cancer Research 7831, vol. 10, 7031-7042, Oct. 15, 2004.

PCT International Search Report for related application PCT/EP2006/060306 dated Jul. 20, 2006, 5 pgs.

"PCT Written Opinion for related application PCT/EP2006/060306 dated Jul. 20, 2006," 5 pgs.

"PCT International Preliminary Report on Patentability for related application PCT/EP2006/060306 dated Sep. 12, 2007," 6 pgs.

"PCT International Search Report for related application PCT/EP2006/060304 dated Jun. 14, 2006," 3 pgs.

"PCT Written Opinion for related application PCT/EP2006/060304 dated Jun. 14, 2006," 5 pgs.

"PCT International Preliminary Report on Patentability for related application PCT/EP2006/060304 dated Jun. 6, 2007," 7 pgs.

"PCT International Search Report for related application PCT/EP2007/054633 dated Jun. 14, 2007," 4 pgs.

"PCT Written Opinion for related application PCT/EP2007/054633 dated Aug. 14, 2007," 5 pgs.

"PCT Demand for related application PCT/EP2007/054633 dated Apr. 9, 2008," 10 pgs.

"PCT International Preliminary Report on Patentability for related application PCT/EP2007/054633 dated Sep. 11, 2008," 7 pgs.

PCT International Search Report for related application PCT/EP2008/053461 dated Oct. 2, 2008, 6 pgs.

"PCT Written Opinion for related application PCT/EP2008/053461 dated Oct. 2, 2008," 10 pgs.

"PCT International Preliminary Report on Patentability for related application PCT/EP2008/053461 dated Oct. 20, 2009," 11 pgs.

"PCT International Search Report for application PCT/EP2004/009723 dated Dec. 7, 2004, from which the instant application is based," 5 pgs.

"PCT Written Opinion for application PCT/EP2004/009723 dated Dec. 7, 2004, from which the instant application is based," 8 pgs.

"PCT Demand for application PCT/EP2004/009723 dated Feb. 14, 2005, from which the instant application is based," 10 pgs.

"PCT International Preliminary Report on Patentability for application PCT/EP2004/009723 dated May 31, 2005, from which the instant application is based" 9 pgs.

"Everyting you ever wanted to know concerning Oligonucleotides but were afraid to ask," downloaded from http://www.auburn.edu/~santosr/protocols/OligoProtocols.pdf, cited Jul. 9, 2010 in corresponding European Patent Application No. 0678537.3, 5 pgs.

Goldschmidt, O. et al., "Cell surface expression and secretion of heparanase markedly promote tumor angiogenesis and metastasis," PNAS, vol. 99, No. 15, Jul. 23, 2002, pp. 10031-10036.

Yang, Y. et al., "Heparanase promotes the spontaneous metastasis of myeloma cells to bone," Blood, vol. 105, No. 3, Feb. 1, 2005, pp. 1303-1309.

Simizu, S. et a., "Heparanase as a molecular target of cancer chemotherapy," Cancer Sci., vol. 96, No. 7, Jul. 2004, pp. 553-558.

Giraud-Panis et al. (Parmacology & Therapeutics 85: 175-181, 2000).

Orsino et al, Childhood acute myelomonocytic leukemia (AML-M4) presenting as catastrophic antiphospholipid antibody syndrome, 2004, Journal of Pediatric Hematology and Oncology, vol. 5, pp. 327-330.

Henning Schroder, "Defibrotide protects endothelial cells, but not L929 tumour cells, from tumour necrosis factor-alpha-mediated cytotosicity," 1995, The Journal of Pharmacy and Pharmacology, vol. 47, pp. 250-252.

Eissner, G. et al, "Oligotide, a defibrotide derivative, protects human microvascular endothelial cells against fludarabine-induced activation, damage and allogenicity," Bone Marrow Transplantation (2005) 35:9, 915-920.

Coccheri, S. et al., "Defibrotide as a Possible Anti-Ischemic Drug," Seminars in Thrombosis and Hemostasis—vol. 22, Supplement 1, 1996, 9-14.

Persengiev, S. et al., "Nonspecific, concentration-dependent stimulation and repression of mammalian gene expression by small interfering RNAs (siRNAs)," RNA Journal (2004) 10:12-18.

Pescador, R. et al., "An Integrated View of the Activities of Defibrotide," Seminars in Thrombosis and Hemostasis—vol. 22, Supplement 1, 1996, 71-75.

Ferrero, M.E. et al., "Efficacy of Defibrotide Treatment in Favoring the Function of the Grafted Heart and Kidney in Rats," Transplantation Proceedings, vol. 26, No. 1 (February), 1994; pp. 251-252.

Marni, A. et al., "Protection of Kidney from Postischemic Reperfusion Injury in Rats Treated with Defibrotide," Transplantation Proceedings, vol. 22, No. 5 (October), 1990; pp. 2226-2229.

Corsi, M. et al., "Antischaemic Effect of Defibrotide Treatment in Rat Kidney," Drugs Exptl. Clin. Res. XIX(6) (1993) 261-265.

Berti, F. et al., "Effects of defibrotide on prostacyclin release from isolated rabbit kidneys and protection from post-ischemic acute renal failure in vivo," Eicosanoids (1991) 4: 209-215.

Comandella, M.G. et al., "Functional and morphological effects of defibrotide on renal ischemia," Res. Exp. Med. (1993) 193: 65-71.

Ferrero, M.E. et al., "Prostacyclin Release from Endothelial Cells, Induced by Defibrotide Treatment, Favours the Function of Grafted Rat Hearts and Kidneys," Int. J. Tiss. Reac. XIII(4) 1991, 215-218.

Corsi, M. et a., "Possible Role of Defibrotide in Endothelial Cell Protection," Int. J. Tiss. Reac. XV(4) 1993, 157-161.

Bianchi, G. et al., "Defibrotide, a Prostacyclin Releasing Agent, Protects the Rabbit Kidney from Acute Failure," Advances in Prostaglandin, Thromboxane, and Leukotriene Research, vol. 21, 1990, pp. 711-714.

Bonomini, V. et al., "Use of Defibrotide in Renal Transplantation in Man," Haemostasis 16: suppl. 1, 1986, pp. 48-50.

* cited by examiner

FORMULATIONS WITH ANTI-TUMOUR ACTION

CROSS REFERENCE TO RELATED APPLICATIONS

This application is a continuation-in-part of and claims priority to prior International Application No. PCT/EP2004/009723, filed Aug. 27, 2004, which claims priority to Italian Application No. MI2003A001714, filed Sep. 5, 2003, and U.S. Provisional Application No. 60/539,344, filed Jan. 28, 2004, the teachings of all of which are incorporated herein by reference.

FIELD OF THE INVENTION

The subject of the present invention is a method for treating a tumor-affected mammal by administering to said mammal an effective amount of defibrotide.

BACKGROUND OF THE INVENTION

The term defibrotide (hereinafter DF) normally identifies a polydeoxyribonucleotide that is obtained by extraction from animal and/or vegetable tissues (1, 2) but which might also be obtained synthetically; the polydeoxyribonucleotide is normally used in the form of an alkali-metal salt, generally a sodium salt, and generally has a molecular weight of about 15-30 kDa (CAS Registry Number: 83712-60-1).

Defibrotide has the following formula of random sequence:

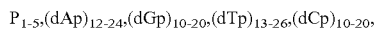

$$P_{1-5},(dAp)_{12-24},(dGp)_{10-20},(dTp)_{13-26},(dCp)_{10-20},$$

wherein
P=phosphoric radical
dAp=deoxyadenylic monomer
dGp=deoxyguanylic monomer
dTp=deoxythymidylic monomer
dCp=deoxycytidylic monomer.

Defibrotide corresponding to this formula shows the following chemico-physical properties: electrophoresis= homogeneous anodic mobility; extinction coefficient, $E_{1cm}^{1\%}$ at $260\pm 1$ nm=$220\pm10°$; extinction reaction, $E_{230}/E_{260}$=$0.45\pm0.04$; coefficient of molar extinction (referred to phosphorus); $\epsilon(P)$=$7.750\pm500$; rotary power $[\alpha]_D^{20°}$=$-53°\pm6$; reversible hyperchromicity, indicated as % in native DNA, h=$15\pm5$; and a purine:pyrimidine ratio of $0.95\pm0.5$.

DF is used mainly on account of its antithrombotic activity (3), although it can be used in other applications such as, for example, the treatment of acute renal insufficiency (4) and the treatment of acute myocardial ischaemia (5). DF is also used in the treatment of emergency clinical conditions, for example, for suppressing the toxicity correlated with high doses of chemotherapy regimens, in particular, the hepatic veno-occlusive syndrome (10, 11); DF has been shown to have protective action towards apoptosis induced by fludarabine and towards the alloactivation of endothelial and epithelial cells, without also altering the antileukaemic effects of fludarabine (12); pre-clinical data also exists on the protective effects of DF that have been achieved in a model of endothelial damage mediated by lipopolysaccharide (13).

A method of producing DF that can produce a product which has uniform and well-defined physical/chemical characteristics and which is also free of possible undesirable side effects is described in U.S. patents (6, 7).

Within the purposes of the present invention DF is either of extractive or of synthetic origin.

DESCRIPTION OF THE INVENTION

In the following study, DF was examined in combination with antiblastic cytotoxic agents in a model of mouse EMT-6 mammary carcinoma cells and in bovine endothelial cells, in cell cultures and in an experimental model in which rats carrying tumours subjected to high doses of chemotherapy were used.

Figure 1:
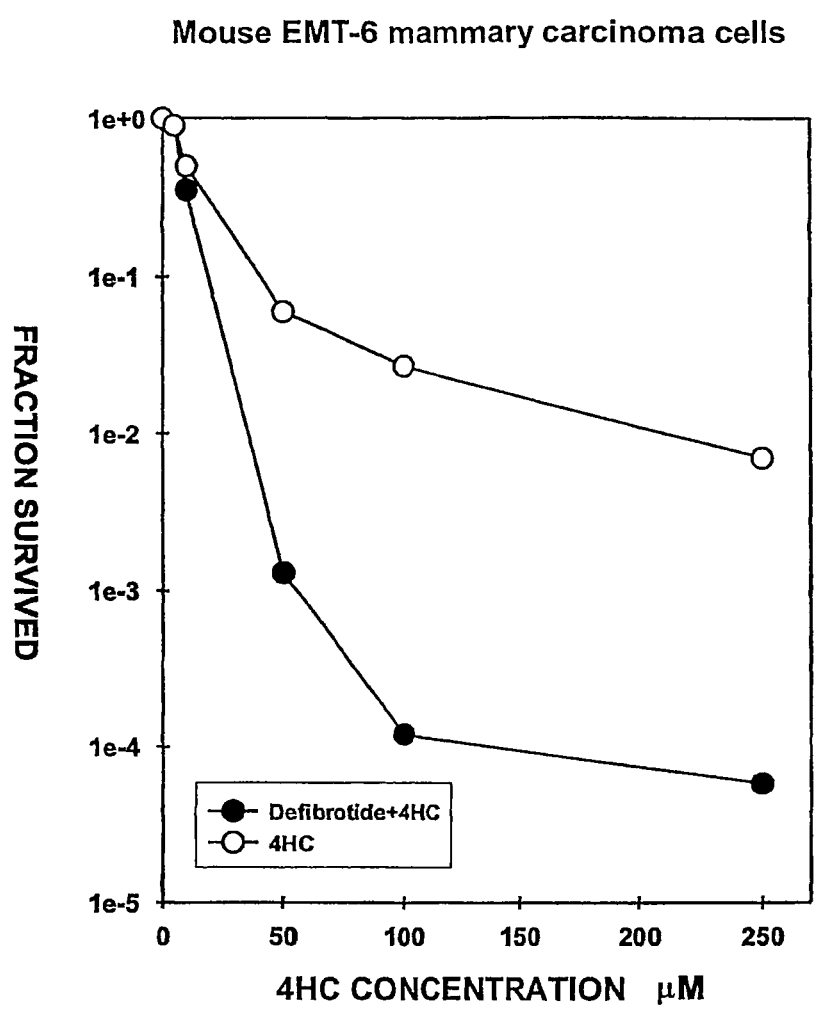
FIG. 1 is a graph of the cytotoxicity of cultured mouse EMT-6 mammary carcinoma cells exposed to 4HC, with and without DF.

Exposure to DF at a concentration of 50 μg/ml, either before and during, or during and after the exposure of mouse EMT-6 mammary carcinoma cells in culture with 4-hydroperoxycyclo-phosphamide (4HC) considerably increases the cytotoxicity of 4HC to the extent of bringing about an increment of 2 logarithmic units in the killing of the tumour cells at 4HC concentrations of between 50 and 250 μmol (see FIG. 1). Exposure to DF at concentrations of 50 μg/ml also leads to an increase in the cytotoxicity of thiotepa with a clear difference based on the method of exposure. In particular, exposure of EMT-6 cells to DF before and during exposure to thiotepa increases cytotoxicity towards the tumour cells by two logarithmic units for thiotepa concentrations of between 100 and 250 μmol. An interesting datum which emerges is that the exposure of EMT-6 cells to DF during and after exposure to thiotepa leads to an increase in cytotoxicity, although to a lesser extent, showing an increase of between 0.5 and 1 logarithmic unit in the cytotoxicity of thiotepa. A similar result has been observed with carboplatin; however, exposure to DF before and during or during and after exposure to melphalan did not show any significant effect on the cytotoxicity of melphalan towards mouse EMT-6 mammary carcinoma cells in culture.

On the other hand, although it was demonstrated that the cytotoxicity of these antiblastic alkylating agents (AA) alone towards bovine endothelial cells in culture was similar to that observed in EMT-6 mammary carcinoma cells, no increase in cytotoxicity was shown when this type of cell culture model was exposed to AAs in association with DF at a concentration of 50 μg/ml.

Figure 2A:
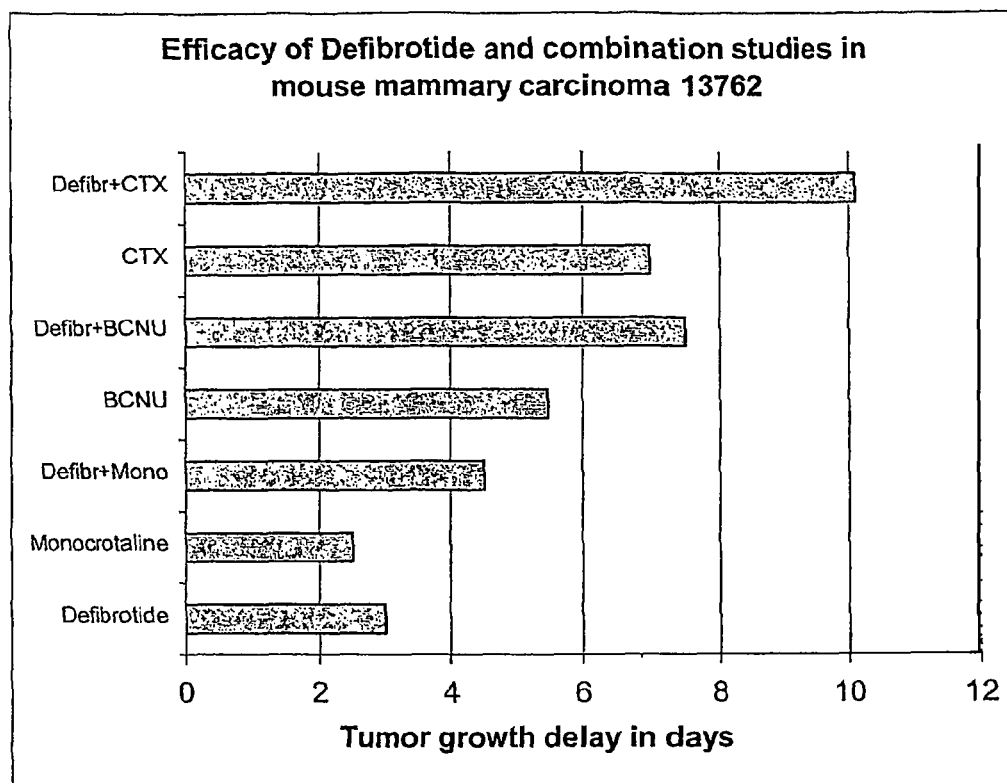
FIG. 2a is a chart of in vivo tumor growth delay in mouse mammary carcinoma 13762 exposed to DF and other agents.
Figure 2B:
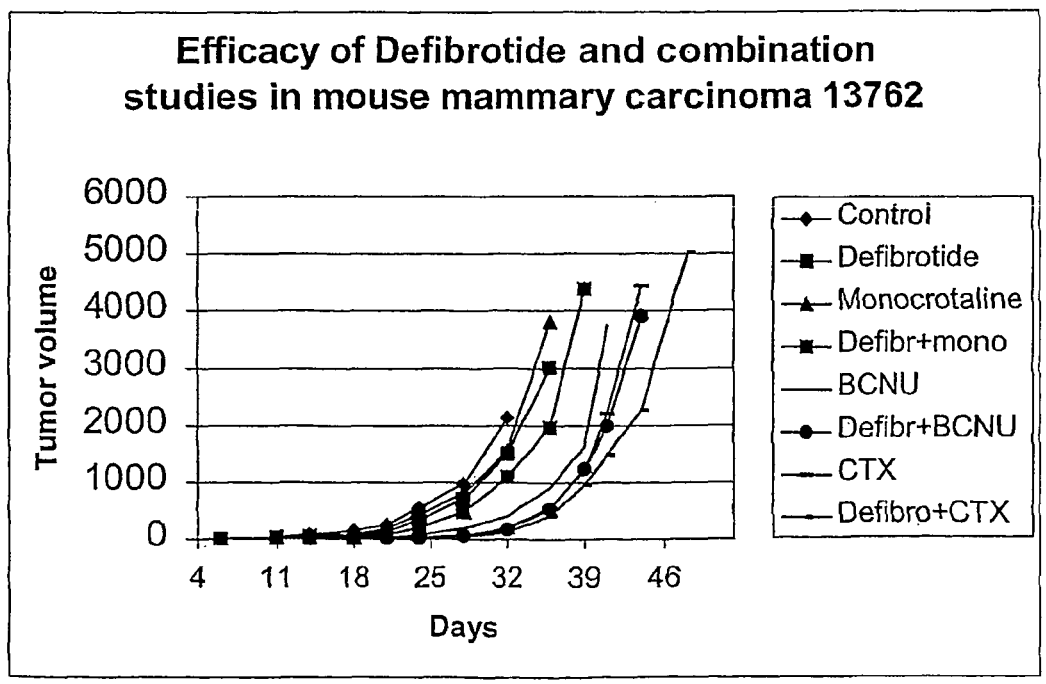
FIG. 2b is a graph of tumor volume in mouse mammary carcinoma 13762 exposed to DF and other agents.

The hepatotoxin monocrotaline and the AA carmustine (BCNU), alone or in association with DF, were tested in vivo in an experimental model which used rats carrying mammary carcinoma 13762. In this experimental model, no additional toxicity was shown in the animals when they were exposed to these agents together with DF, but a significant tumour growth delay (TGD) was observed (see Table 1 and FIGS. 2a and 2b).

Table 1. Tumour growth delay in rats carrying mammary carcinoma 13762 after treatment with monocrotaline or BCNU, alone or in association with defibrotide (DF). The tumour was implanted on day 0 and the chemotherapy was administered on day 8 and day 18.

| Treatment Group | Days to reach 500 mm³ | TGD (days) | p Value |
|---|---|---|---|
| Controls | 14.6 ± 0.8 | — | — |
| Monocrotaline (350 mg/kg) ip days 8 & 18 | 15.6 ± 1.0 | 1.0 | 0.435 |
| DF (200 mg/kg) iv twice per day, days 8–26 + Monocrotaline | 16.1 ± 0.6 | 1.5 | 0.134 |
| DF (200 mg/kg) iv twice per day, days 10–26 + Monocrotaline | 18.2 ± 1.5 | 3.6 | 0.034 |
| BCNU (150 mg/kg) ip days 8 & 18 | 18.0 ± 2.5 | 3.4 | 0.195 |
| DF (200 mg/kg) iv twice per day, days 8–26 + BCNU | 19.7 ± 1.5 | 5.1 | 0.003 |
| DF (200 mg/kg) iv twice per day, days 10–26 + BCNU | 21.3 ± 1.6 | 6.7 | 0.0002 |

These studies have been reproduced with the use of monocrotaline, BCNU, and cyclophosphamide (CTX), alone or in combination with DF, in the same experimental model. In comparison with the control, a significant tumour growth delay (TGD) was observed with the use of DF alone (p<0.05); this delay was particularly significant when DF was associated with CTX and BCNU (p<0.04) and was notably greater than that obtained by the individual use of each agent. Unexpectedly, when DF was used alone, at first it delayed the growth of the tumour but afterwards tumour growth became normal again. Moreover, when DF was used in combination with an AA, the tumour regrowth became rapid as soon as the co-administration of DF ceased. This data suggests not only an additional anti-tumour effect of DF but also a direct antiblastic activity of DF itself.

A reduction in tumour growth (TGD) and in the number of pulmonary metastases was also observed in mice carrying Lewis pulmonary carcinoma when DF was added to treatment with paclitaxel, whether or not it was associated with carboplatin and in comparison with cytotoxic therapy alone, but without showing an obvious increase in toxicity (data not presented). The mechanism underlying these effects remains to be explained, but it is possible that the anti-adhesive properties of DF are involved, given the role of cell adhesion in the mechanisms implicated in drug resistance (8, 9).

It was also tested whether DF has in vivo activity in a murine model of human multiple myeloma (MM). Sixty male SCID/NOD mice (6-8 weeks old) were irradiated (450 rads) and, 24 hrs later, injected s.c. with 5×10 6 MM-1S human MM cells. Upon formation of palpable tumors, mice were randomly assigned to 6 cohorts (10 mice each) receiving a) vehicle; b) DF (i.v. 450 mg/kg b.i.d); c) melphalan (MEL) 2.5 mg/kg i.p. once weekly; d) cyclophosphamide (CTX) 50 mg/kg i.p., on days 8, 10, 12, 20, 22 and 24; e) and f) combinations of DF (300 mg/kg i.v.) with MEL or CTX, respectively. Mice were monitored q3 days for body weight, potential toxicity, and electronic caliper-based tumor volumes.

DF, either as single agent or in combination with MEL or CTX, was well tolerated without hemorrhagic complications or body weight loss (P>0.05) in all groups. The major endpoints for efficacy were a) tumor volume changes and b) overall survival (time-to-sacrifice, performed when tumor diameters>2 cm). DF treatment resulted in significantly lower tumor volumes than in control mice (P<0.05 for all comparisons by analysis of variance and post-hoc tests); in combination with MEL or CTX it induced significantly lower tumor volumes than the respective single-agent cytotoxic chemotherapy (P<0.05 for all comparisons). Kaplan-Meier survival analyses showed that DF administration, either as single agent or in combination with cytotoxic chemotherapy (MEL or CTX), was associated with statistically significant prolongation of overall survival, in comparison to vehicle-treated control group or MEL- or CTX-treated groups, respectively (P<0.001 for all comparisons, log-rank test). Interestingly, the in vitro studies have not shown a significant direct in vitro cytotoxic effect of DF against MM cells, suggesting that the observed in vivo activity may be due to effect(s) on interactions of MM cells with their local microenvironment.

These promising results demonstrate that DF does confer tumor protection in this MM chemotherapy model and constitutes the first proof-of-principle that DF not only has in vivo anti-tumor activity against MM but also enhances responses to cytotoxic treatment. This study suggests that the anti-MM activity of DF is possibly due to its effects on MM cell interactions with their microenvironment and provides a framework for future clinical trials of DF in combination with other agents for the treatment of MM and other neoplasias.

A method for treating a tumor-affected mammal, preferably a human, by administration of an effective amount of DF is therefore an object of the present invention. DF may be administered in combination with at least another active ingredient with anti-tumour action. The other active ingredient with anti-tumour action may be selected from paclitaxel, monocrotaline, BCNU, melphalan and/or cyclophosphamide.

A method for treating a tumor-affected mammalian, preferably a human, by administration of an effective amount of DF is therefore an object of the present invention. DF may be administered in combination with at least another active ingredient with anti-tumour action. The other active ingredient with anti-tumour action may be selected from paclitaxel, monocrotaline, BCNU, melphalan and/or cyclophosphamide.

Further objects of the invention are represented by the formulations containing DF and at least one other active ingredient with anti-tumour action; the formulations will preferably be in the form of aqueous solutions and, even more preferably, suitable for intravenous administration, and may contain the excipients and coadjuvants known in the art.

For the purposes of the present invention, the term defibrotide (DF) should thus be understood as any oligonucleotide and/or polynucleotide produced by extraction from animal and/or vegetable tissues, in particular, from mammalian organs. Preferably, the DF will be produced in accordance with the method described in U.S. patents (6, 7) which are incorporated herein by reference.

BIBLIOGRAPHY

1. U.S. Pat. No. 3,770,720
2. U.S. Pat. No. 3,899,481
3. U.S. Pat. No. 3,829,567
4. U.S. Pat. No. 4,694,134
5. U.S. Pat. No. 4,693,995
6. U.S. Pat. No. 4,985,552
7. U.S. Pat. No. 5,223,609
8. Carlo-Stella, C., Di Nicola, M., Magni M., et al., Defibrotide in Combination with Granulocyte Colony-stimulating Factor Significantly Enhances the Mobilization of Primitive and Committed Peripheral Blood Progenitor Cells in Mice. Cancer Research, 2002, 62:6152-6157 (Nov. 1, 2002).
9. Hazlehurst, L., Damiano, J., Buyuksal, I., Pledger, W. J., Dalton, W. S., Adhesion to fibronectin via b1 integrins regulates p27 kip1 levels and contributes to cell adhesion mediated drug resistance (CAM-DR). Oncogene, 2000; 19:4319-4327.
10. Richardson, P. G., Elias, A. D., Krishnan, A., et al. Treatment of severe veno-occlusive disease with defibrotide: compassionate use results in response without significant toxicity in a high-risk population. Blood, 1998; 92: 737-44.
11. Richardson, P., Murakami, C., Jin, Z., et al., Multi-institutional use of defibrotide in 88 patients after stem cell transplantation with severe veno-occlusive disease and multi-system organ failure: response without significant toxicity in a high risk population and factors predictive of outcome. Blood, 2002; 100(13):4337-4343.
12. Eissner, G., Multhoff, G., Gerbitz, A., et al., Fludarabine induces apoptosis, activation, and allogenicity in human endothelial and epithelial cells: protective effect of defibrotide. Blood, 2002; 100:334-340.
13. Falanga, A., Vignoli, A., Marchetti, M., Barbui, T., Defibrotide reduces procoagulant activity and increases fibrinolytic properties of endothelial cells. Leukemia, 2003; in press.

The invention claimed is:

1. A method for treating a human affected by multiple myeloma, said method consisting essentially of administering to said human an effective amount of defibrotide sufficient to treat the multiple myeloma, the defibrotide obtained by extraction from animal tissue and having CAS registry number 83712-60-1.

2. A method according to claim 1, wherein defibrotide is administered intravenously.

3. A method according to claim 1, wherein the defibrotide comprises an oligonucleotide and/or polynucleotide extracted from animal tissue.

4. A method according to claim 1, wherein the defibrotide comprises a polydeoxyribonucleotide obtained by extraction from animal tissue, in the form of an alkali-metal salt.

5. A method for treating a human affected by multiple myeloma, said method consisting essentially of administering to said human an effective amount of defibrotide sufficient to treat the multiple myeloma, the defibrotide obtained by extraction from animal tissue and comprising a polydeoxyribonucleotide corresponding to the following formula of random sequence:

$$P_{1-5},(dAp)_{12-24},(dGp)_{10-20},(dTp)_{13-26},(dCp)_{10-20},$$

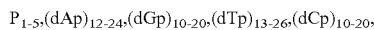

Wherein
P=phosphoric radical
dAp=deoxyadenylic monomer
dGp=deoxyguanylic monomer
dTp=deoxythymidylic monomer
dCp=deoxycytidylic monomer,
with the following chemico-physical properties:
electrophoresis=homogeneous anodic mobility;
extinction coefficient, $E_{1cm}^{1\%}$ at 260±1 nm=220±10°;
extinction reaction, $E_{230}/E_{260}$=0.45±0.04;
coefficient of molar extinction (referred to phosphorus), $\epsilon(P)$=7.750±500;
rotary power $[\alpha]_D^{20°}$=53°±6;
reversible hyperchromicity, indicated as % in native DNA, h=15±5; and
a purine:pyrimidine ratio of 0.95±0.5.

6. A method according to claim 5, wherein defibrotide is administered intravenously.

7. A method according to claim 5 wherein the defibrotide comprises an oligonucleotide and/or polynucleotide.

8. A method according to claim 5 wherein the defibrotide comprises a polydeoxyribonucleotide obtained by extraction from animal tissue, in the form of an alkali-metal salt.

9. A method according to claim 1 wherein the method consists of administering to said human an effective amount of defibrotide sufficient to treat the multiple myeloma, the defibrotide obtained by extraction from animal tissue and having CAS registry number 83712-60-1.

10. A method for treating a human affected by multiple myeloma, said method comprising administering to said human an effective amount of defibrotide sufficient to treat the multiple myeloma, the defibrotide obtained by extraction from animal tissue and having CAS registry number 83712-60-1.

11. A method according to claim 10, wherein defibrotide is administered intravenously.

12. A method according to claim 10 wherein the defibrotide comprises an oligonucleotide and/or polynucleotide extracted from animal tissue.

13. A method according to claim 10 wherein the defibrotide comprises a polydeoxyribonucleotide obtained by extraction from animal tissue, in the form of an alkali-metal salt.

14. A method according to claim 10 wherein the defibrotide comprises a polydeoxyribonucleotide corresponding to the following formula of random sequence:

$$P_{1-5},(dAp)_{12-24},(dGp)_{10-20},(dTp)_{13-26},(dCp)_{10-20},$$

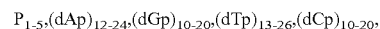

Wherein
P=phosphoric radical
dAp=deoxyadenylic monomer
dGp=deoxyguanylic monomer
dTp=deoxythymidylic monomer
dCp=deoxycytidylic monomer,
with the following chemico-physical properties:
electrophoresis=homogeneous anodic mobility;
extinction coefficient, $E_{1cm}^{1\%}$ at 260±1 nm=220±10°;
extinction reaction, $E_{230}/E_{260}$=0.45±0.04;
coefficient of molar extinction (referred to phosphorus), $\epsilon(P)$=7.750±500;
rotary power $[\alpha]D^{20°}$53°±6;
reversible hyperchromicity, indicated as % in native DNA, h=15±5; and
a purine:pyrimidine ratio of 0.95±0.5.

* * * * *